United States Patent [19]
Wolf et al.

[11] Patent Number: 5,741,656
[45] Date of Patent: Apr. 21, 1998

[54] EPSTEIN-BARR VIRUS SEQUENCES ENCODING A DIAGNOSTICALLY RELEVANT VIRUS CAPSID ANTIGEN, EXPRESSION CLONES DERIVED THROUGH POLYMERASE CHAIN REACTION AND THE USE OF THIS RECOMBINANT ANTIGEN IN DIAGNOSTIC TESTS

[75] Inventors: Hans Joachim Wolf, Josef-Jagerhuber-Strasse 9, 82319 Starnberg; Udo Reischl, Grafenau; Manfred Motz, Munich, all of Germany

[73] Assignee: Hans Joachim Wolf, Starnberg, Germany

[21] Appl. No.: 586,640

[22] PCT Filed: Jul. 22, 1994

[86] PCT No.: PCT/EP94/02436

§ 371 Date: Apr. 29, 1996

§ 102(e) Date: Apr. 29, 1996

[87] PCT Pub. No.: WO95/03415

PCT Pub. Date: Feb. 2, 1995

[30] Foreign Application Priority Data

Jul. 23, 1993 [EP] European Pat. Off. ............... 93111883

[51] Int. Cl.$^6$ ............... G01N 33/53; G01N 33/48; C12P 21/00; C12P 19/34
[52] U.S. Cl. ............... 435/7.1; 435/69.3; 435/8; 435/91; 435/172.3; 436/63
[58] Field of Search ............... 435/69.3, 6, 7.1, 435/91, 172.3; 436/63

[56] References Cited

U.S. PATENT DOCUMENTS 4,683,195  7/1987  Mullis ............... 435/6

FOREIGN PATENT DOCUMENTS

| 0173254 | 3/1986 | European Pat. Off. | ......... C12N 15/00 |
| 0574048 | 12/1993 | European Pat. Off. | ......... C12N 15/38 |
| WO A 91 02091 | 2/1991 | WIPO | ............... C12Q 1/68 |
| WO A 91 08224 | 6/1991 | WIPO | ............... C07K 7/06 |
| WO A 91 09127 | 6/1991 | WIPO | ............... C12N 15/38 |

OTHER PUBLICATIONS

Baer et al 1984 Nature 310 p. 207, Jul. 19, 1984.
Beisel et al. 1985 J Virology 54 (3) p. 665, Jun. 1, 1985.
Biggin et al 1984 EMBO 3 (5) p. 1083, May 1, 1984.

*Primary Examiner*—Michael P. Woodward
*Assistant Examiner*—Mary K. Zeman
*Attorney, Agent, or Firm*—John P. White

[57] ABSTRACT

The application describes the identification of Epstein-Barr virus (EBV) encoded gene and rapid methods for construction of plasmids efficiently expressing this or other genes. The EBV gene can be purified and used as an antigen for diagnosis and therapy of EBV related diseases.

6 Claims, 11 Drawing Sheets

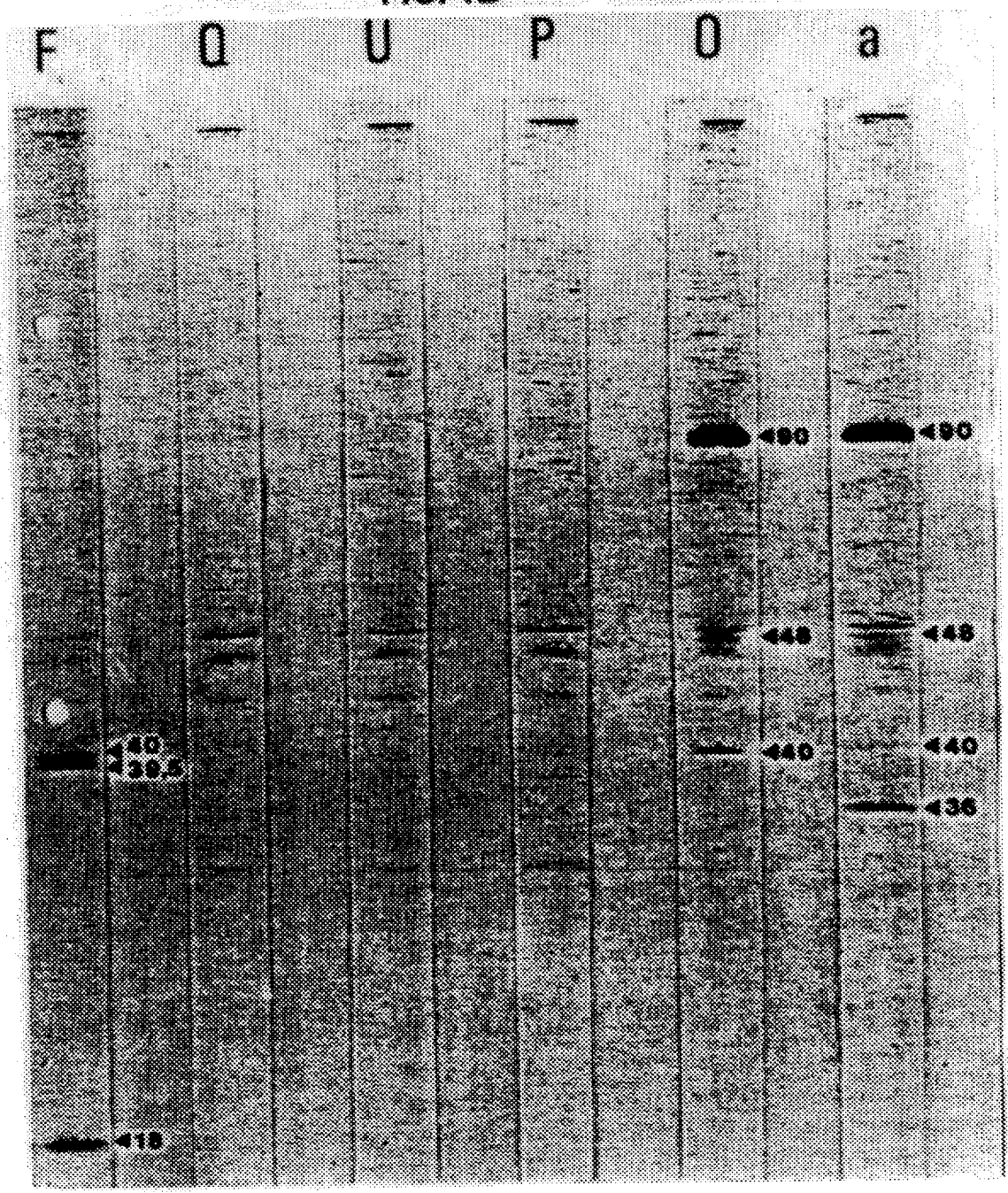

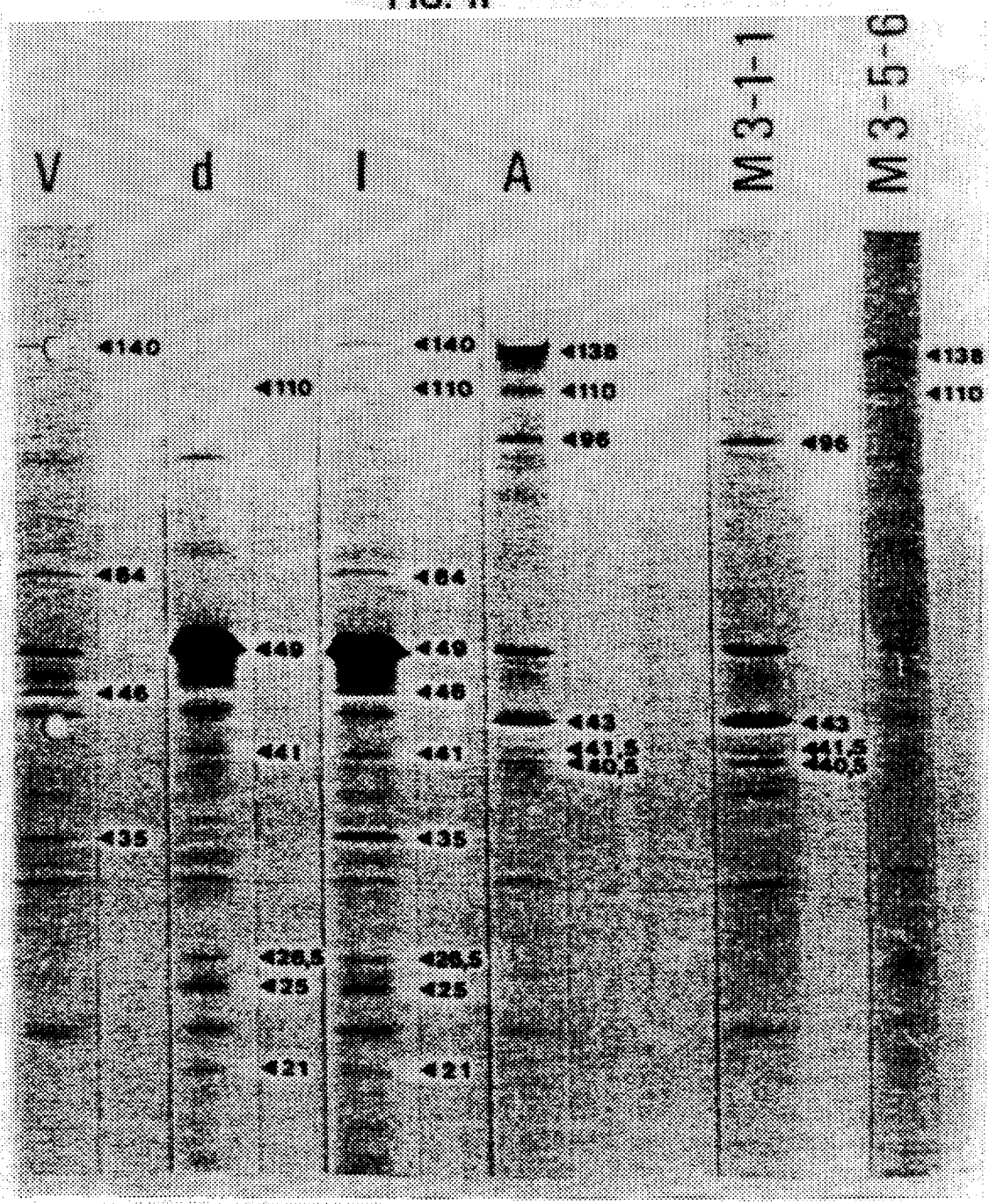

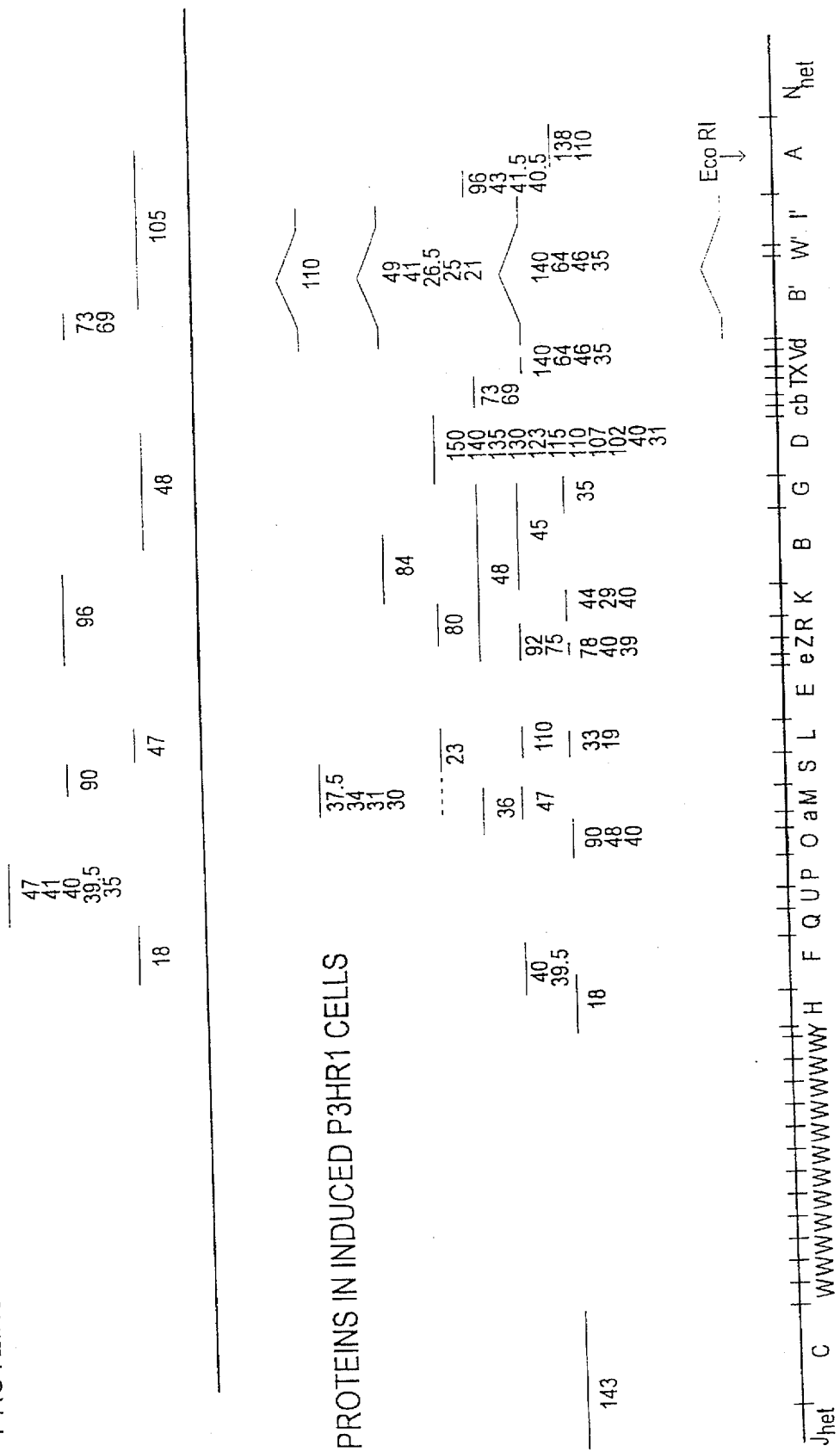

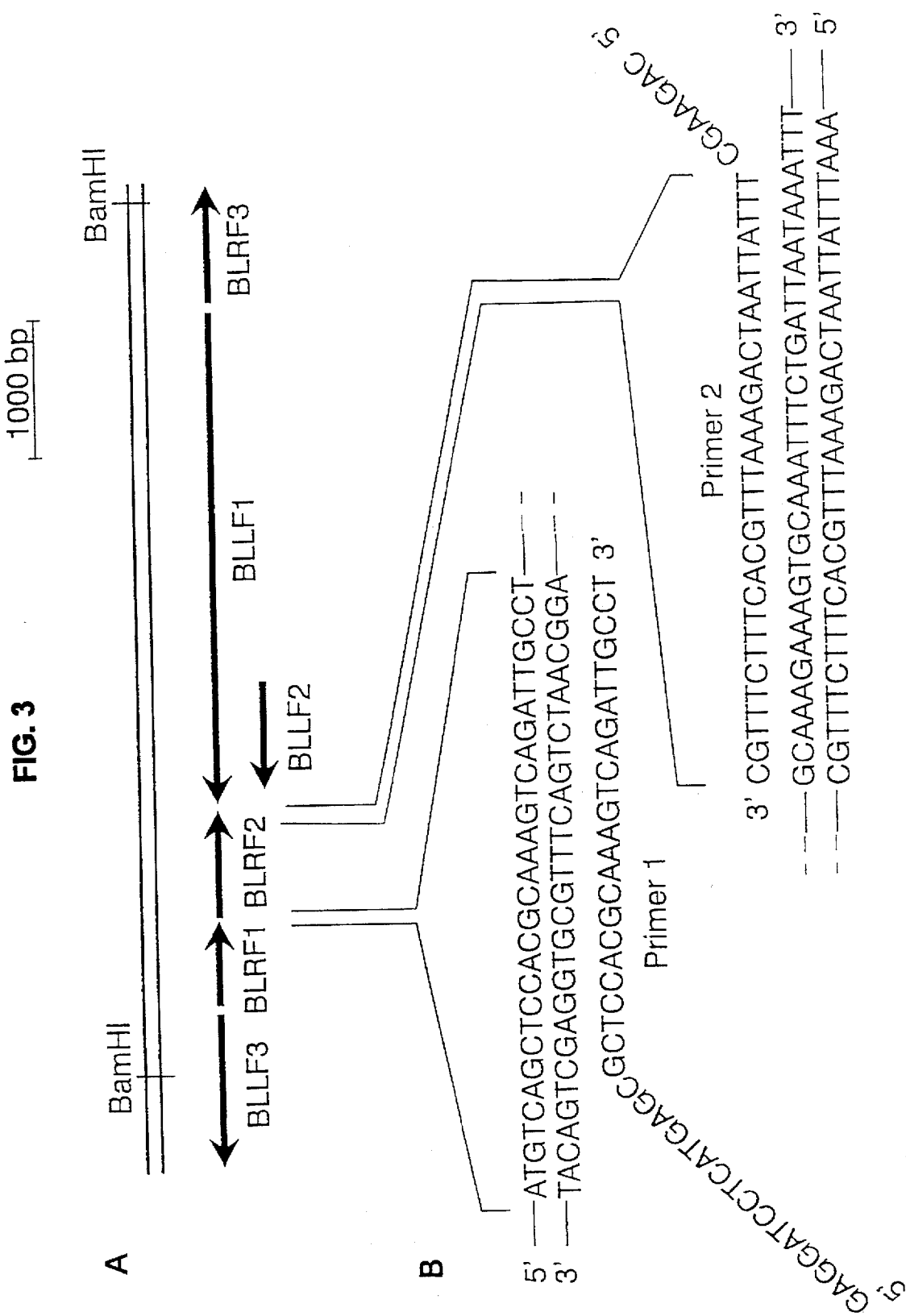

FIG. 6

```
ATGTCAGCTCCACGCAAAGTCAGATTGCCTTCTGTTAAGGCTGTTGACATGAGCATGGAA
---------+---------+---------+---------+---------+---------+
MetSerAlaProArgLysValArgLeuProSerValLysAlaValAspMetSerMetGlu

GACATGGCCGCCCGCCTGGCTCGCCTGGAGTCTGAGAATAAGGCTCTGAAGCAACAGGTC
---------+---------+---------+---------+---------+---------+
AspMetAlaAlaArgLeuAlaArgLeuGluSerGluAsnLysAlaLeuLysGlnGlnVal

CTCAGAGGGGGTGCCTGTGCCTCGTCTACCTCTGTTCCTTCTGCTCCAGTGCCTCCGCCT
---------+---------+---------+---------+---------+---------+
LeuArgGlyGlyAlaCysAlaSerSerThrSerValProSerAlaProValProProPro

GAGCCGCTTACAGCTCGACAGCGAGAGGTAATGATTACGCAGGCCACGGGCCGTTTGGCG
---------+---------+---------+---------+---------+---------+
GluProLeuThrAlaArgGlnArgGluValMetIleThrGlnAlaThrGlyArgLeuAla

TCTCAGGCTATGAAGAAGATTGAAGACAAGGTTCGGAAATCTGTTGACGGTGTAACTACC
---------+---------+---------+---------+---------+---------+
SerGlnAlaMetLysLysIleGluAspLysValArgLysSerValAspGlyValThrThr

CGCAATGAAATGGAAAATATATTGCAAAATCTGACCCTCCGCATTCAAGTATCTATGTTG
---------+---------+---------+---------+---------+---------+
ArgAsnGluMetGluAsnIleLeuGlnAsnLeuThrLeuArgIleGlnValSerMetLeu

GGTGCAAAAGGCCAACCCAGCCCTGGTGAGGGAACACGACCACGAGAATCAAACGACCCC
---------+---------+---------+---------+---------+---------+
GlyAlaLysGlyGlnProSerProGlyGluGlyThrArgProArgGluSerAsnAspPro

AACGCCACCCGACGTGCCCGCTCCCGCTCCCGGGGACGTGAAGCAAAGAAAGTGCAAATT
---------+---------+---------+---------+---------+---------+
AsnAlaThrArgArgAlaArgSerArgSerArgGlyArgGluAlaLysLysValGlnIle

TCTGATTAA
---------
SerAspEnd
```

EPSTEIN-BARR VIRUS SEQUENCES ENCODING A DIAGNOSTICALLY RELEVANT VIRUS CAPSID ANTIGEN, EXPRESSION CLONES DERIVED THROUGH POLYMERASE CHAIN REACTION AND THE USE OF THIS RECOMBINANT ANTIGEN IN DIAGNOSTIC TESTS

TECHNICAL FIELD OF INVENTION

This invention relates to a DNA sequence of the EBV genome coding for an EBV-related antigen that can be used in methods and diagnostic and pharmaceutical compositions referred to below and methods of localizing and isolating at least part of the respective DNA sequences. Furthermore, this invention relates to methods and compositions or kits, respectively, for a rapid, simple, very sensitive and highly specific determination of antibodies directed to this EBV-related antigen. In these tests said antigen of EBV essentially improves the detection of specific antibody classes in the patient sera. This detection allows reliable conclusions as to the status of infection of the donor such as preinfection, fresh infection, chronic infection, convalescence and neoplastic condition.

BACKGROUND ART

Epstein-Barr-Virus (EBV) Infections and Their Consequences

EBV causes infectious mononucleosis as a primary disease. Predominantly it affects children or young adults. More than 90% of the average adult population is infected by EBV that persists lifelong in its carriers. The virus is produced lifelong in the oropharynx and spreads via the oral route. Whereas infection of young children often leads to almost symptom free seroconversion, infection of adults often causes serious diseases with high fever, dramatic increases in white blood cell count, sore throat, enlarged liver and spleen. Scarlet fever, toxoplasmosis, diphteria and leukemia have to be discriminated by diagnostic means.

Chronic Infections

Rarely does EBV infection lead to chronic or chronically fluctuating symptoms comparable to the acute primary infection.

Hairy Leukoplakia

In immunocompromised patients EBV can cause serious lesions on the tongue.

Reactivation of EBV in Immunologically Deprived Individuals

Depression of cell mediated immunity leads to reactivation of EBV. Increased antibody titers are a consequence and detrimental effects of multiple possible sources such as transplant rejection have been described.

X-linked Proliferative Syndrome

Certain genetic constellations are responsible for infection of male siblings leading to fatal lymphoreticular disease.

Burkitt's Lymphoma and EBV

The development of Burkitt's lymphoma is linked to chromosomal rearrangements. Not all cases contain EBV genomes in the tumor cells. However, at least in areas with high incidence, 97% of these neoplasias are EBV-related and a control of EBV infection is likely to reduce the risk of developing Burkitt's lymphoma.

Nasopharyngeal Carcinoma as a Possible "Secondary Disease" Related to EBV

The other disease where EBV shows a 100% association is nasopharyngeal carcinoma (NPC) ("The Biology of Nasopharyngeal Carcinoma", UICC technical report series, vol. 71, M. J. Simons and K. Shanmugaratnam (eds), International Union Against Cancer, Geneva, p. 1 (1982)). NPC most frequently starts at the fossa of Rosenmueller (*Recessus pharyngeus*) at the postnasal space. Frequently patients are hospitalized only after the first typical metastases have developed in the cervical lymph nodes.

Control of EBV-Related Neoplasia

There are three possible basic strategies to control neoplasia:

1. Early detection followed by therapy,
2. delay of onset of disease ideally beyond the average lifespan, and
3. prevention.

These goals may be achieved also in multifactorial diseases such as many neoplasias. Incidence of disease may be reduced by eliminating one or more of the essential factors which are not necessarily capable by themselves to cause the disease, or by reducing factors which promote the manifestation of neoplastic conditions. The use of the specific virus-related antigens of this invention, antibodies or genetic materials as tools for early diagnosis of virus-related tumors, might facilitate the elimination of essential factors.

Use of EBV-Related Gene Products for Diagnosis of EBV-Related NPC

Before recombinant antigens with defined composition became available, the most common virus specific serological tests were based on immunofluorescence tests using EBV genome positive cells with various properties and/or pretreatment as source of usually cell-associated antigens in immunofluorescence or immunoenzymatic tests. Table I gives a summary of the antibody disease and vital antigens usable for diagnosis.

TABLE I

Correlation of EBV-caused diseases and Ig-subclass specific antibody reaction as can be determined by conventional immunofluorescence tests.

| Disease: | VCA IgG | IgM | IgA | EA IgG | EBNA IgG | MA[1] IgG |
|---|---|---|---|---|---|---|
| Normal Adults | + | − | − | − | + | − |
| Acute Adults (early) | ++ | + | − | + | − | − |
| Chronic infection | + | + | − | +/− | +/− | +/−? |
| Reactivation | + | + | − | + | + | + |
| XLP[2] | + | − | − | +/− | (+) | ? |
| NPC | ++ | − | + | +(D) | + | ++ |
| BL | ++ | − | − | +(R) | + | + |

VCA: viral capsid antigen; EA: early antigen; EBNA: Epstein-Barr nuclear antigen;
[1]determined by immunoprecipitation of gp240/200;
[2]XLP as an example of immunologically deprived hosts.

Presently used EBV derived antigens are not recognized by all EBV infected persons due to restrictions of the immune response. Furthermore, some EBV related antigens share sequence homology on the protein level with other Herpes viruses. Thus, the technical problem underlying the present invention is to provide an EBV related protein that permits a more reliable diagnosis of EBV infection. The solution of the above mentioned technical problem is achieved by providing the embodiment characterized in the claims. Accordingly the present invention provides an EBV-encoded probe without major genetic variability.

BRIEF SUMMARY OF INVENTION

Production of EBV-Specific Antigens According to the Present Invention

1. As a consequence of all findings, it is one of the objects of this invention to improve the sensitivity of tests for detection of antibody classes and specific antibodies to virus capsid class of antigens and to improve a system which allows mass testing and better standardization.

2. The application of recombinant DNA technology has made possible the identification of a polypeptide important for improvement of EBV antigenicity. Production could be achieved by appropriate host cells transformed with recombinant DNA molecules and grown in appropriate culture systems.

3. According to the present invention, recombinant DNA methods, including a selection of modified primers for polymerase chain reaction, are used to express the genetic information of the gene or at least parts of the gene encoding the EBV protein 23 kDa (reading from BLLF2) in appropriate host cells such as bacteria (e.g. the genera *E. coli*, Salmonella, Pseudomonas or Bacillus), yeasts (e.g. genera Candida or Saccharomyces), insect cells (e.g. *Spodoptera frugiperda* SF251) and mammalian cells (e.g. Vero-cells, CHO-cells or lymphoblastoid cell lines).

4. Furthermore, the genomic regions encoding the EBV protein 23 kDa were identified and their relevance for diagnostic purposes demonstrated. Therefore, the key information for the production of these proteins or antigenic determinants thereof is also disclosed in the present invention.

The DNA sequence hybridizes to a DNA sequence from whatever source obtained, including natural, synthetic or semisynthetic sources, which is related by mutations, including nucleotide substitutions, nucleotide deletions, nucleotide insertions and inversions of nucleotide stretches to a DNA sequence which encodes at least part of a protein related to the 23 kDa protein encoded by the reading frame BLRF2 of the B95-8 protein of Epstein-Barr virus. Preferably the hybridization conditions are in the range of 15°–27° C. below the melting point of the homodimeric DNA molecule. The present invention relates to the production of an EBV-specific antigen by recombinant DNA technology and its use in diagnosis, prophylaxis and therapy of EBV-related diseases. Therefore, it is an object of this invention to identify a novel Epstein-Barr viral antigen, which is correlated with Epstein-Barr virus related diseases like nasopharyngeal carcinoma (NPC), infectious mononucleosis and Burkitt's lymphoma (see legend to Table I) by immunological methods. Another object of this invention is the localization and identification of genomic regions of EBV, for example as it has been cloned from B95-8 cells (American Type Culture Collection, Rockville, Md. USA (ATCC) CRL1612) (Skare, J., and Strominger, J. L. Cloning and mapping of BamHI endonuclease fragments of the DNA from the transforming B95-8 strain of Epstein-Barr virus. Proc. Natl. Acad. Sci. USA 77:3860 (1980)), which code for said antigens of diagnostic importance and of relevance for medical purposes. This is achieved by using the hybrid selection method combined with immune precipitation with patient sera (FIG. 1). A further object of the present invention is the subcloning of a genomic region of EBV, e.g. from existing libraries of EBV, cloned from B95-8 cells which encodes at least a part of the useful antigen p23. This is achieved by polymerase chain reaction (PCR), which amplifies genomic DNA fragments without requiring suitable restriction enzyme cleavage sites at the ends of the reading frame and inserting such amplified genes containing synthesized ends from the primer sequences following appropriate cloning procedures into expression plasmids. It is evident that the same cloning procedure can be done by amplifying the desired gene from other viral isolates which may differ from B95-8 coding sequences. Other primers may be necessary for that purpose, the selection and production of which is state of the art. The selection of primers with additional sequences 5' of the sequences complementary to the coding region (5' primers) or 3' of the sequences complementary to the coding regions is possible without the need for extensive subcloning to establish clones directly from the polymerase chain reaction product which are optimized for expression by additional control signals. Another object of this invention is the production of proteins by expression of the respective genetic information in suitable host cells, such as bacteria (e.g. of the genera Escherichia, Salmonella, Pseudomonas or Bacillus), yeasts (e.g. of the genera Candida or Saccharomyces), animal cells and human cells (e.g. Vero-cells; CHO-dhfr-cells; in combination with an appropriate selection system, optionally a plasmid carrying a functional dhfr gene as well as the genetic information for the EBV gene under control of a suitable regulation sequence; or lymphoblastoid cell lines). The proteins produced by these host cells contain 23 kDa-related antigenic determinants (epitopes) and are, depending on the expression system, synthesized either as a fusion protein or a non-fusion protein. For the production of a fusion protein by bacteria the expression of the genomic subfragments encoding p23 of EBV B95-8 was introduced into the known plasmid pUC8 and was induced e.g. by isopropyl-β-D-thiogalactopyranoside (IPTG). The respective expression products were identified by immunological methods. For the production of non-fusion proteins which essentially contain amino acid sequences of the naturally occurring proteins or parts thereof the recombinant plasmids of the present invention may be modified. If an oligonucleotide linker is inserted between the bacterial protein encoding region and the EBV-related protein encoding region of the expression vector, the amino acid sequence corresponding to the oligonucleotide linker becomes part of the expressed fusion protein. After isolation of this fusion protein from the transformants expressing it, it is cleaved either by amino acid sequence specific proteases in the introduced amino acid linker or, if the amino acid linker comprises peptide bonds sensitive to acid cleavage, by treatment with acids, e.g. formic acid.

A further object of the present invention is the utilization of the EBV-related protein 23 kDa or subregions thereof or, if suitable, EBV-related DNA fragments or clones, for the production of diagnostic compositions (kits) useful in clinical diagnosis or scientific research. These tests are based on established principles such as ELISA, RIA (Radio immunoassay) or the indirect hemagglutination assay. Furthermore, the EBV-related protein can be used, e.g for monitoring vaccination programs, analyzing epidemological problems, for patient treatment (component of medication) and for the production of vaccines as a prophylactic measure in the therapy of EBV-related diseases, such as mononucleosis, Burkitt's lymphoma and nasopharyngeal carcinoma. Finally, this protein is useful for prophylaxis and therapy of EBV-related diseases, because it is able to modulate the immune response in patients suffering from diseases such as NPC, chronic infectious mononucleosis or EBV-related Burkitt's lymphoma.

BRIEF DESCRIPTION OF THE DRAWINGS

FIG. 2: Fine mapping of mRNAs relative to the EBV B95-8 genome. The BamHI restriction sites of the EBV B95-8 genome are given at the bottom of the figure and the respective restriction fragments are designated by upper and lower case letters. The mRNAs of the proteins localized by hybrid-selection to individual BamHI restriction fragments are indicated by numbers and lines. It can be taken from the fine mapping that antibodies to 23 kDa are present in EBV-convalescent sera.

FIG. 3: A) Localization of reading frames in the BamHI-L fragment. An EBV-antigen with a size of 23 kDa was mapped by hybrid selected translation. BLLF1 encodes the EBV major membrane antigen, BLLF2, BLRF1 and BLRF3 encode proteins with calculated molecular weights of 31.11 kDa and 12 kDa. BLLF3 also maps in the neighboring BamHI-S fragment, whereas the 23 kDa antigen coding region was found only in BamHI-L. Therefore, the most probable candidate for encoding the 23 kDa antigen seem to be the BLRF2 encoded protein. B) Enlargement of the 5' and 3' end of BLRF2 with both strands and the oligodeoxynucleotide primers used in PCR. Primer 1 hybridizes to the DNA sequences encoding the N-terminus of the 23-kDa protein. The complementary sequence starts after the second codon. The region around the translational start was changed into a BspHI site for cloning into an ATG-expression vector. This includes the change of the second codon from TCA to AGC both encoding serine. The oligodeoxynucleotide sequence upstream from the ATG start codon encodes the BamHI restriction enzyme site and a few additional nt to facilitate restriction enzyme digestion and cloning. Primer 2 hybridizes at the translational stop of the 23-kDa and contains a HindIII site at its 5' end for insertion into vectors. Both non-hybridizing 5' ends of the primers are not synthesized during the first PCR round on the complementary strand but within the following rounds when the new generated PCR products are used as template.

FIG. 6: DNA and amino acid sequence of the 23 kDa antigen from reading frame BLRF2 of Epstein-Barr virus.

The examples illustrate the invention.

EXAMPLE 1

Amplification of the 23 kDa protein encoding region. The possible coding region for the 23 kDa protein (BLRF2) on the BamHI-L fragment of EBV contains 162 amino acids. No suitable restriction enzyme sites at the 5' and 3' ends are available for direct cloning of the full length reading frame. For this reason we synthesized two oligodeoxynucleotides complementary to the 5' and 3' ends of the coding region and used them as primers in PCR. Each primer contains additional sequences at the 5' end for restriction sites useful in cloning the amplified DNA (FIG. 1) and a few additional nucleotides to facilitate the cutting with these restriction enzymes. Following PCR the amplified DNA segments were cleaved with BamHI and HindIII, purified by agarose gel electrophoresis and used for cloning with plasmid vectors. A plasmid containing the entire BamHI-L fragment from the B95-8 isolate of EBV (Skare, J. and Strominger, J. L. Cloning and mapping of BamHI endonuclease fragments of the DNA from the transforming B95-8 strain of Epstein-Barr virus. Proc. Natl. Acad. Sci. USA 77:3860 (1980)) was used as template.

EXAMPLE 2

Figure 1A:
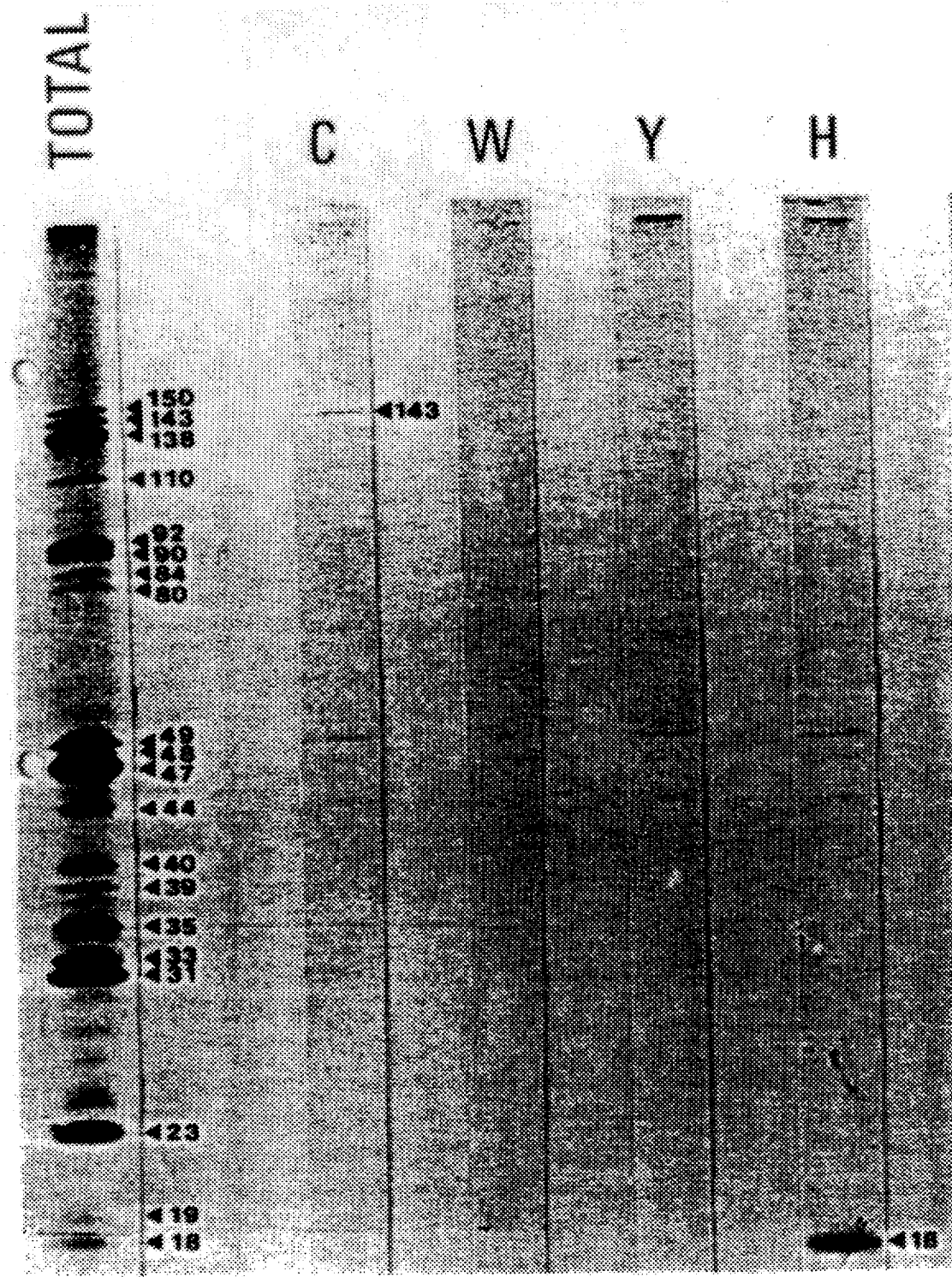
FIG. 1: Autoradiography of in vitro translation products from RNA hybrid selected with BamHI DNA fragments of the EBV genome. For immunoprecipitation a pool of EBV-specific sera derived from patients suffering from NPC was used. The immunoprecipitated $^{35}$S-labelled proteins were separated by a SDS-polyacryamide gel electrophoresis and X-ray film was exposed to the gel. The control, designated "pool", contains all of the immunoprecipitable EBV-specific proteins. It can be taken from the autoradiography that antibodies to 23 kDa are present in EBV-positive sera. It is also evident that RNA from phorbol ester induced P3HR1 cells was hybridized against BamHI restriction fragments of EBV DNA, eluted and translated in vitro. The translation products were immunoprecipitated with a pool of EBV reactive sera preadsorbed with EBV genome negative BJAB cells, as described earlier (Seibl, R. and Wolf H. Mapping of Epstein-Barr virus proteins on the genome by translation of hybrid-selected RNA from induced P3HR1 cells and induced Raji cells. Virology 141:1–13 (1985)).
Figure 1C:
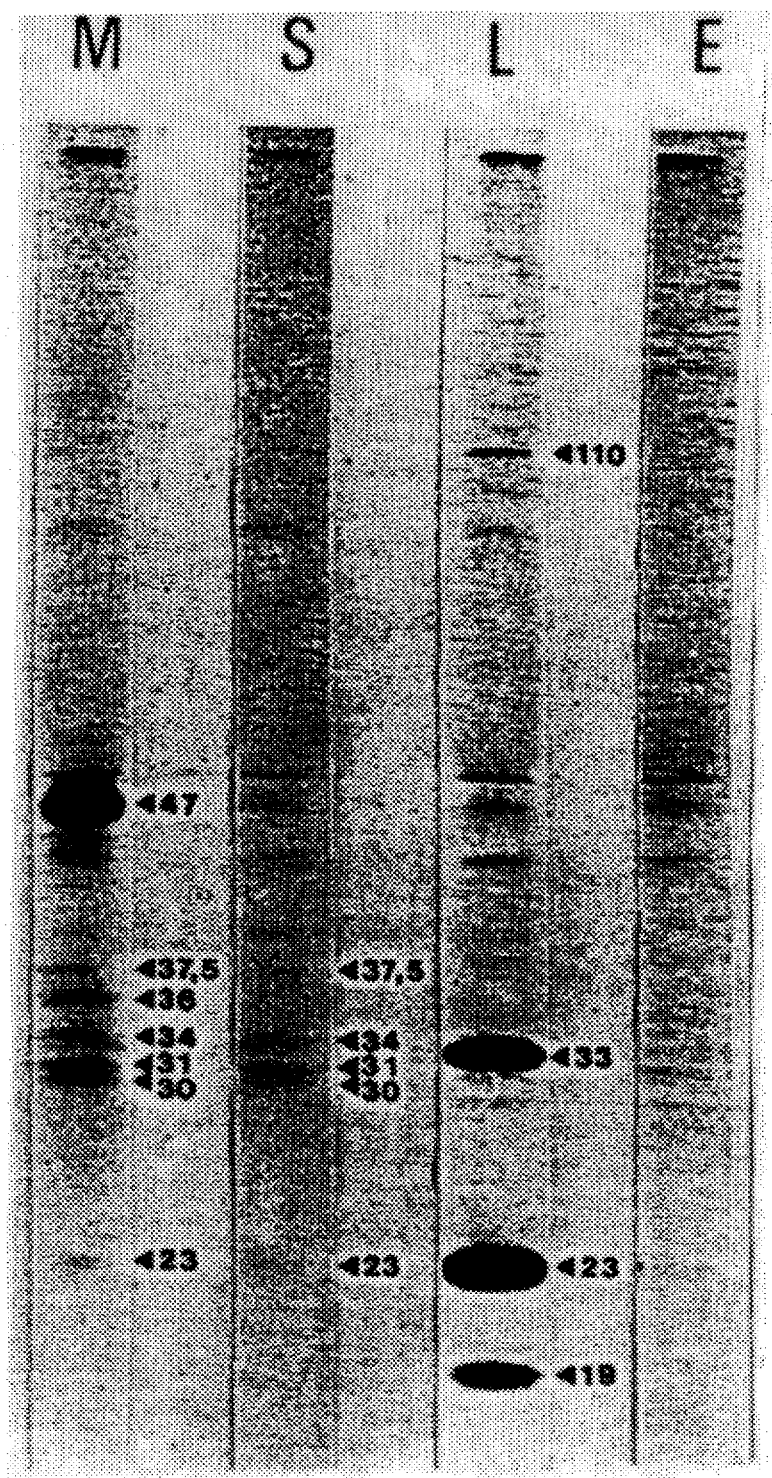
Figure 1D:
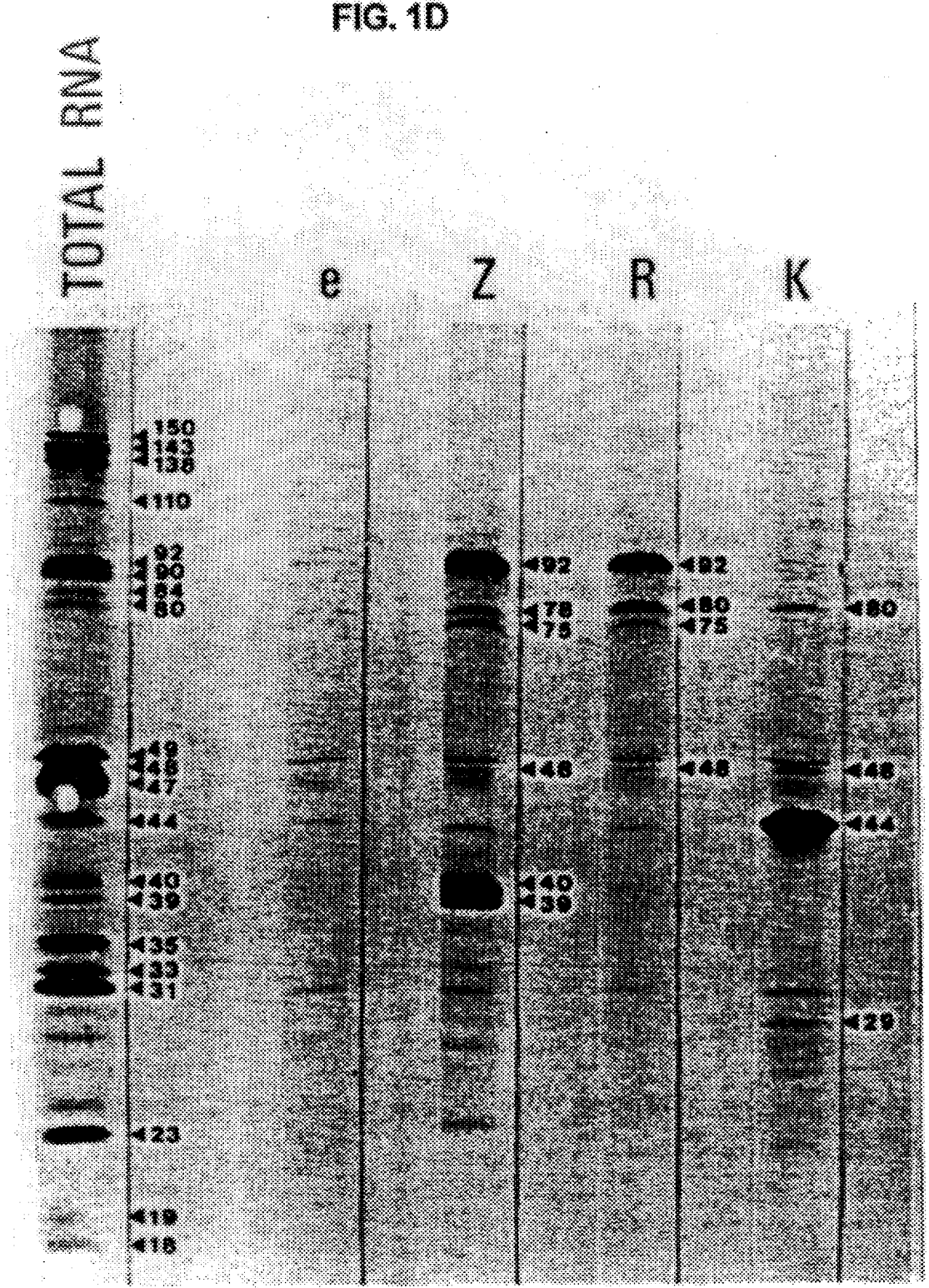
Figure 1E:
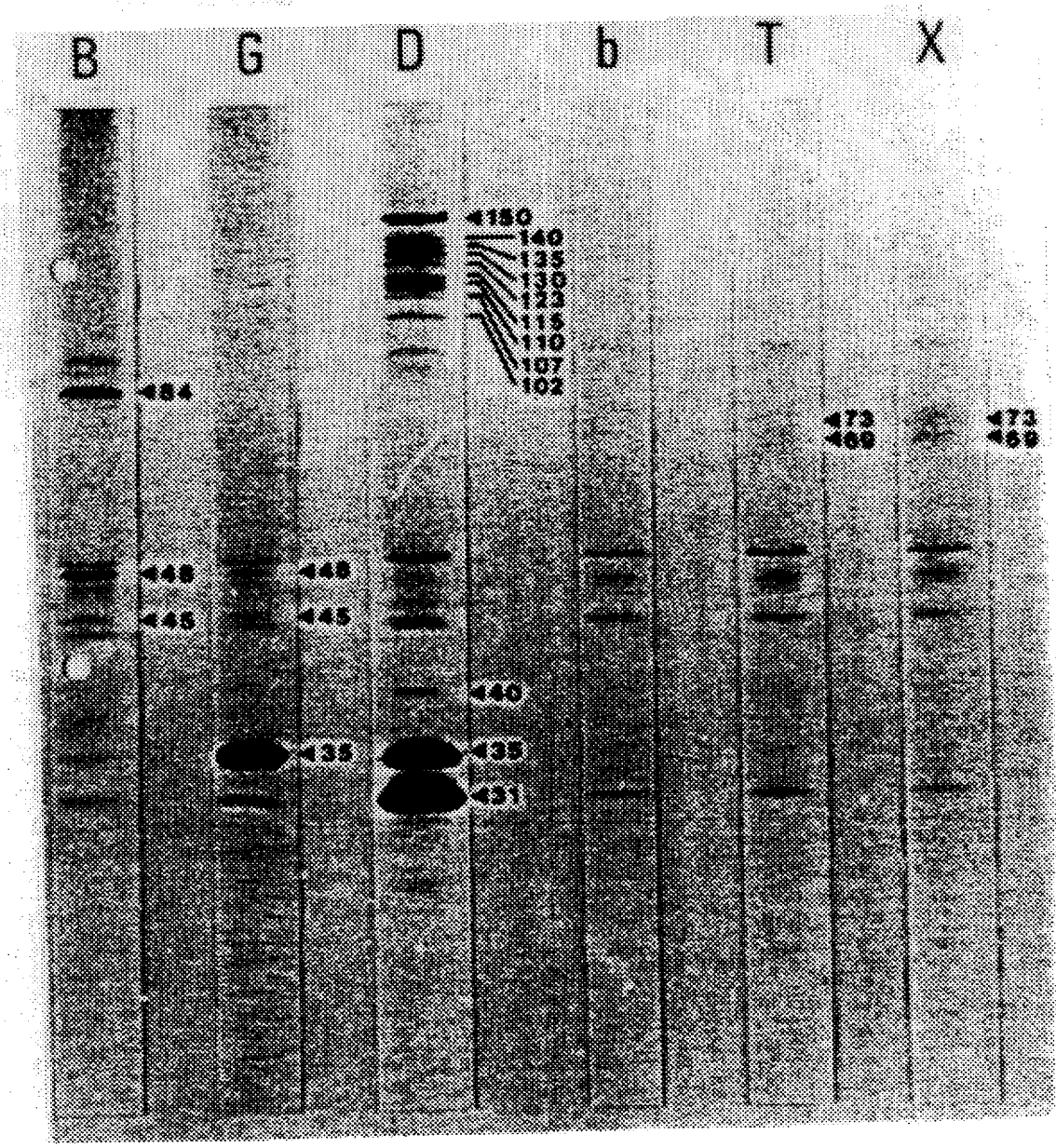
Figure 4:
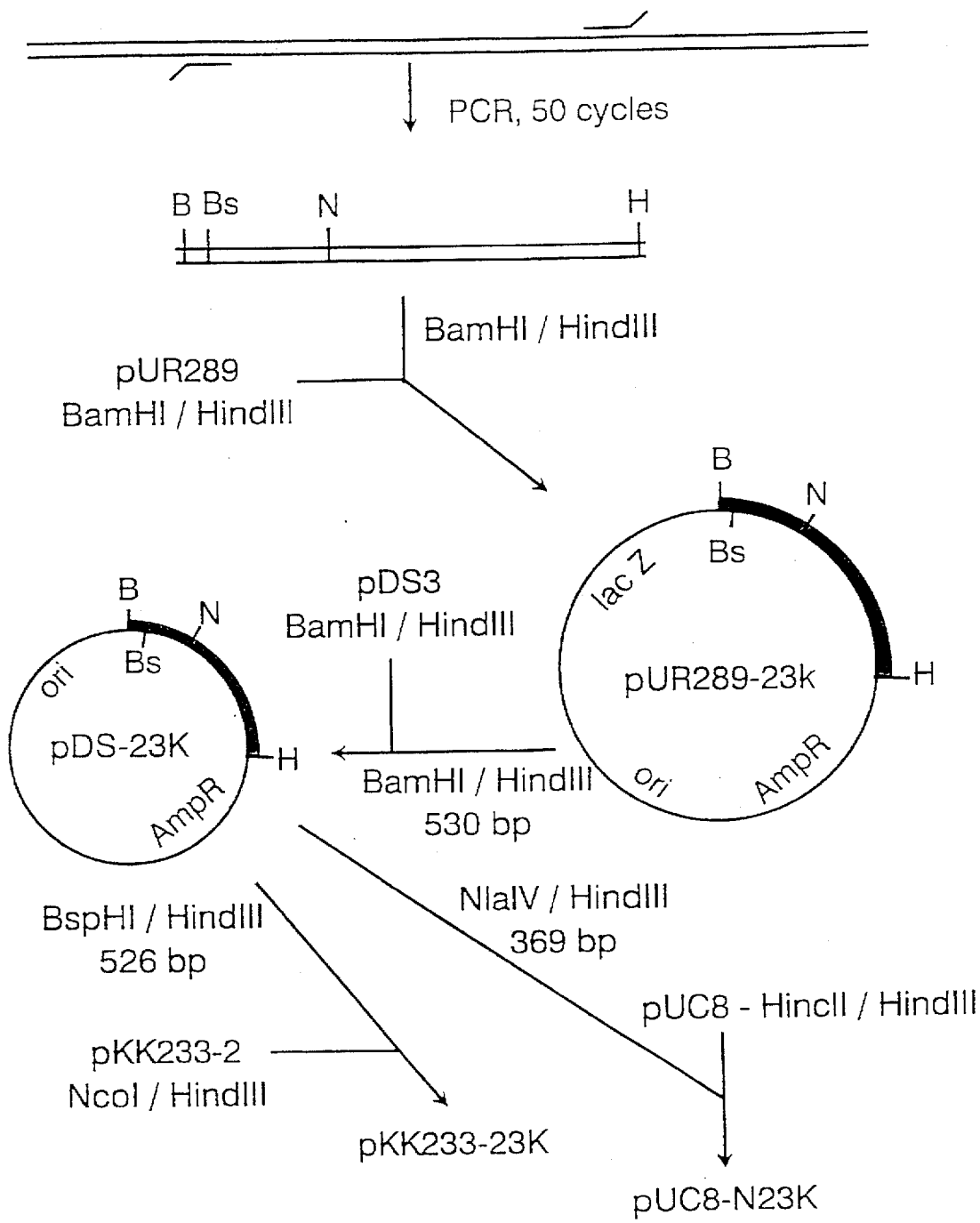
FIG. 4: Generation of amplified DNA and cloning. The oligodeoxynucleotide primers shown in 1(B) were synthesized on an 8700 DNA synthesizer (Biosearch/MILLIGEN) in 1 mol columns. Since synthesis was very efficient, the primers were used without further purification in PCR after cleavage from the column. Five PCR reactions in parallel containing the same composition with 100 µl each were performed with 0.25% of the total primer yield, 4 ng of a plasmid containing the BamHI-L fragment of EBV (Skare, J. and Strominger, J. L. Cloning and mapping of BamHI endonuclease fragments of the DNA from the transforming B95-8 strain of Epstein-Barr virus. Proc. Natl. Acad. Sci. USA 77:3860 (1980)), nucleotides, buffer and Taq-polymerase according to manufacturer's instructions. The reaction was performed in an Ericomp temperature cycle with 50° C. annealing temperature for 2 min, elongation at 72° C. for 4 min and 1 min at 94° C. for denaturation. Fifty cycles were run, the resulting DNA collected, precipitated by ethanol and dried. After resuspension in 200 1 H$_2$O the DNA was digested with BamHI and HindIII. The DNA fragments were purified through 1.5% agarose gel electrophoresis, isolated and ligated with pUR289 linearized with BamHI in HindIII. After transformation into E. coli JM109 (Yanish-Perron et al. Improved M13 phage cloning vectors and host strains nucleotide sequences of M13mp18 and pUC19 vectors. Gene 33:103–119 (1985)) the plasmids of colonies were screened for the 23 kDa antigen encoding fragment by restriction enzyme digest. The production of the EBV antigen was visualized by IPTG induction of positive clones, PAGE of proteins and either Coomassie blue staining or Western blots (FIG. 5). From a producing clone, pUR23k, the 23 kDa encoding segment was again isolated by digest with BamHI and HindIII and inserted into pDS (pD523k). In a third step, the fragment was isolated by BspHI and HindIII cleavage and ligated with pKK233-2 linearized with NcoI and HindIII (pKK23k). Finally, from pDS23k a NlaIV/HindIII fragment with 370 bp was obtained and ligated with pUC8 linearized with HindII and HindIII pUC8-N234. All described expression cloning procedures provide an in frame translational function from the vector sequences into the EBV derived fragment.
Figure 5A:
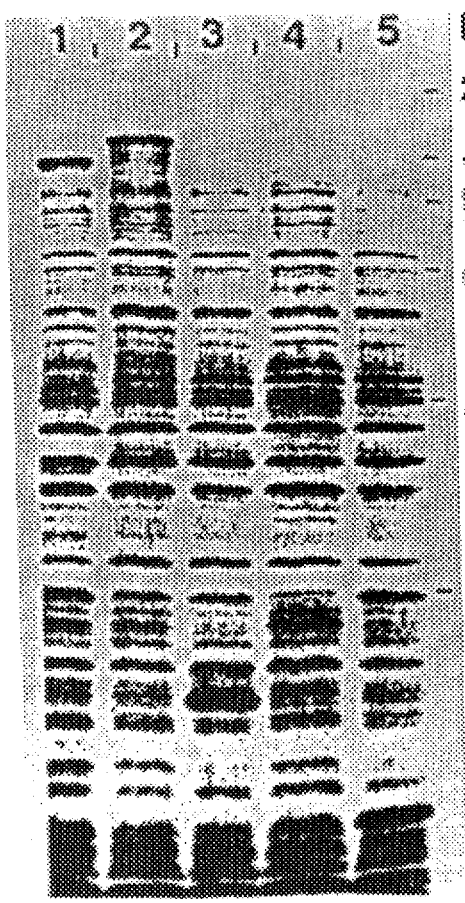
FIG. 5: Identification of 23 kDa expression product in E. coli. The proteins of the IPTG induced clones (1 mM IPTG for 3 h at 37° C.) were analyzed by SDS-17.5 PAGE and Coomassie blue staining (left panel) or via Western blot and immunostaining with a high-titered serum pool from NPC patients. Lane 1: pUR289, β-Gal expression; lane 2: pUR23k; lane 3: pDS23k; lane 4: pKK23k; lane 5: pUCN23k. The β-Gal::23 kDa fusion protein in lane 2 is larger than the β-Gal in lane 1 (116 kDa) indicating a read-through of the amplified DNA fragment. The 23 kDa expression product in lane 3 has a size of about 24 kDa and is synthesized to a high extent. However, the authentic 23 kDa expression product from the ATG vector in lane 4 is not produced efficiently. The C-terminal 23 kDa antigen fragment from pUCN23 in lane 5 seems to be stable and is produced very efficiently. All antigens react with the NPC serum pool quite strongly indicating the antigenicity of this protein during virus infection.
Figure 5B:
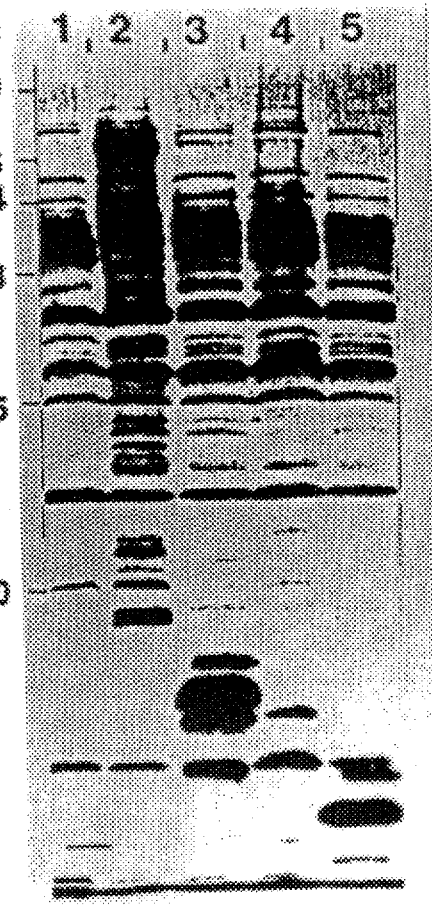

Expression of 23 kDa VCA in E. coli as a β-galactosidase fusion protein. Since many recombinant antigens are not stably expressed as non-fusion antigens in *E. coli*, first evaluations were made by producing β-galactosidase fusion proteins where the large bacterial protein theoretically prevents unstable protein segments from degradation. For this reason the amplified DNA digested with BamHI and HindIII was cloned in frame 3' of the lacZ gene of the βGal expression vector pUR289 (Rüther and Müller-Hill, Easy identification of cDNA clones. EMBO J. 2 (1983) 1791–1794) (FIG. 4). An *E. coli* clone containing this vector was induced with IPTG in order to express the βGal::23 kDa fusion protein. FIG. 5 demonstrates that a product with a molecular weight higher than the authentic βGal has been synthesized. The fusion protein reacts specifically with a serum containing high EBV antibody titers. This indicates that a correct translation has occurred, no major errors or stop codons have been introduced by PCR and that an immunogenic EBV antigen is produced.

EXAMPLE 3

Expression of 23 kDa VCA as an authentic protein. From pUR289-23k the EBV coding region was isolated with BamHI and HindIII and cloned pDS12/RBSII-2 which has been renamed pDS3 for this presentation (Bujard, H. et al. The T5 promotor-based transcription translation system for the analysis in vitro and in vivo. Meth. Enzymol. 155:416 (1987)) which supplies the same translational frame as is given in the 23 kDa coding region (FIG. 4). After induction with IPTG a new protein band with 23 kDa appears in Coomassie-stained PAGE. It reacts specifically with EBV serum on Western blots and represents about 10% of the total *E. coli* protein as can be estimated from the Coomassie-stained gel (FIG. 5). Since the expression product contains a few amino acids derived from the cloning site and oligodeoxynucleotide sequences, an expression of the authentic protein was achieved by isolating this fragment with BspHI and HindIII and inserting it into the NcoI and HindIII sites of the ATG vector pKK233-2 (Amann, E. and Brosius, J. 'ATG vectors' for regulated high-level expression of cloned genes in *Escherichia coli*. Gene 40:183–190 (1985)). However, the expression yield of the 23 kDa antigen from this vector was much lower than from the pDS vector, may be due to an ineffective translation of this protein in the *E. coli* cells caused by the altered N-terminal sequence. A further expression was achieved from a smaller fragment encoding the C-terminal part of 23 kDa antigen. From the coding region a NlaIV/HindIII fragment was isolated and inserted into HindII/HindIII of pUC8 (Vieira, B. and Messing, B. The pUC plasmids, a M13mp7-derived system for insertion mutagenesis and sequencing with synthetic universal primers. Gene 19 (1982) 259–268) in order to produce pUCN23k. Again a very efficient antigen production was found after IPTG induction. But since this antigen does not contain the N-terminus of the authentic protein it was not used for further evaluations.

EXAMPLE 4

Reactivity and specifity of the 23 kDa VCA. The initial evaluation of the diagnostic value of the recombinant antigen was conducted with EBV positive and negative sera obtained from various serum sources, i.e. patients with infectious mononucleosis, patients suffering from NPC and healthy carriers. Crude bacterial lysates containing the 23 kDa antigen from pDS23k, and lysates with no foreign antigen as controls were run separately on PAGE. The proteins were transferred to nitrocellulose filters and strips thereof were incubated with sera. The results of the immunostained Western blot strips are summarized in Table II. By comparison with conventional immunofluorescence tests VCA positive sera from healthy carriers and NPC patients were clearly positive for the 23 kDa antigen Only two sera reactive in the IF test showed no reaction. Three sera from freshly infected persons as determined from the IF also showed no reaction, and three sera believed to be EBV negative were found to be positive with the p23 kDa antigen. To summarize, a broad correlation of IF and Western blot activity can be seen. However, further testing is necessary to examine the relevance and sensitivity of this antigen in comparison with IF tests.

TABLE II

Reactivity of the 23kDa antigen with various sera in comparison to IF results.

| IF-reactivity | EBV status[a] | nr. of sera tested | Reactivity with recombinant 23k antigen[b] | |
|---|---|---|---|---|
| | | | pos | neg |
| VCA+ EBNA+ | healthy carrier | 34 | 32 | 2 |
| VCA+ EBNA+ | NPC patient | 4 | 4 | 0 |
| VCA+ EBNA− | fresh infection | 9 | 6 | 3 |
| VCA− EBNA− | EBV negative | 6 | 3 | 3 |

[a]The EBV status was determined by routine diagnostics with IF reactivity and additional clinical data.
[b]Reactivity of the 23kDa antigen was examined by Western blot analysis.

Classification of the sera according to IF tests was: VCA+, EBNA+=healthy carrier; VCA+, EBNA+clinical data=NPC; VCA+, EBNA−, clinical data=fresh infection; VCA−, EBNA−=negative for EBV.

We claim:

1. A method for the detection of EBV infections comprising obtaining a sample from serum of a patient, and determining the content of sera against the p23kDA antigen of EBV, the determined presence and amount of sera being indicative of the presence of an EBV infection.

2. The method according to claim 1 which comprises:

(a) obtaining a serum sample of the subject;

(b) incubating the serum sample with a membrane to which the EBV 23 kDA antigen is adsorbed;

(c) detecting bound antibodies via immunostaining of the membrane.

3. The method according to claim 1, wherein the EBV 23 kDa antigen has the sequence of SEQ ID NO: 2.

4. The method according to claim 1, 2 or 3, characterized in that the presence of positive sera is determined in an immunodiagnostic method.

5. The method according to claim 4, wherein the immunodiagnostic method is selected from the group consisting of immunofluorescence test VCA, ELISA, RIA, and indirect hemagglutination assay.

6. A diagnostic composition for carrying out the method according to any one of claims 1–5, comprising at least one protein having the sequence of SEQ ID NO: 2.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:

( A ) LENGTH: 489 base pairs ( B ) TYPE: nucleic acid ( C ) STRANDEDNESS: single ( D ) TOPOLOGY: linear ( i i ) MOLECULE TYPE:

(ix) FEATURE:
    (A) NAME/KEY: CDS
    (B) LOCATION: 1..486

(xi) SEQUENCE DESCRIPTION: SEQ ID NO: 1:

| ATG | TCA | GCT | CCA | CGC | AAA | GTC | AGA | TTG | CCT | TCT | GTT | AAG | GCT | GTT | GAC | 48 |
|---|---|---|---|---|---|---|---|---|---|---|---|---|---|---|---|---|
| Met | Ser | Ala | Pro | Arg | Lys | Val | Arg | Leu | Pro | Ser | Val | Lys | Ala | Val | Asp | |
| 1 | | | | 5 | | | | | 10 | | | | | 15 | | |

| ATG | AGC | ATG | GAA | GAC | ATG | GCC | GCC | CGC | CTG | GCT | CGC | CTG | GAG | TCT | GAG | 96 |
|---|---|---|---|---|---|---|---|---|---|---|---|---|---|---|---|---|
| Met | Ser | Met | Glu | Asp | Met | Ala | Ala | Arg | Leu | Ala | Arg | Leu | Glu | Ser | Glu | |
| | | | 20 | | | | 25 | | | | | 30 | | | | |

| AAT | AAG | GCT | CTG | AAG | CAA | CAG | GTC | CTC | AGA | GGG | GGT | GCC | TGT | GCC | TCG | 144 |
|---|---|---|---|---|---|---|---|---|---|---|---|---|---|---|---|---|
| Asn | Lys | Ala | Leu | Lys | Gln | Gln | Val | Leu | Arg | Gly | Gly | Ala | Cys | Ala | Ser | |
| | | 35 | | | | | 40 | | | | | 45 | | | | |

| TCT | ACC | TCT | GTT | CCT | TCT | GCT | CCA | GTG | CCT | CCG | CCT | GAG | CCG | CTT | ACA | 192 |
|---|---|---|---|---|---|---|---|---|---|---|---|---|---|---|---|---|
| Ser | Thr | Ser | Val | Pro | Ser | Ala | Pro | Val | Pro | Pro | Pro | Glu | Pro | Leu | Thr | |
| 50 | | | | | 55 | | | | | 60 | | | | | | |

| GCT | CGA | CAG | CGA | GAG | GTA | ATG | ATT | ACG | CAG | GCC | ACG | GGC | CGT | TTG | GCG | 240 |
|---|---|---|---|---|---|---|---|---|---|---|---|---|---|---|---|---|
| Ala | Arg | Gln | Arg | Glu | Val | Met | Ile | Thr | Gln | Ala | Thr | Gly | Arg | Leu | Ala | |
| 65 | | | | 70 | | | | | 75 | | | | | 80 | | |

| TCT | CAG | GCT | ATG | AAG | AAG | ATT | GAA | GAC | AAG | GTT | CGG | AAA | TCT | GTT | GAC | 288 |
|---|---|---|---|---|---|---|---|---|---|---|---|---|---|---|---|---|
| Ser | Gln | Ala | Met | Lys | Lys | Ile | Glu | Asp | Lys | Val | Arg | Lys | Ser | Val | Asp | |
| | | | | 85 | | | | | 90 | | | | | 95 | | |

| GGT | GTA | ACT | ACC | CGC | AAT | GAA | ATG | GAA | AAT | ATA | TTG | CAA | AAT | CTG | ACC | 336 |
|---|---|---|---|---|---|---|---|---|---|---|---|---|---|---|---|---|
| Gly | Val | Thr | Thr | Arg | Asn | Glu | Met | Glu | Asn | Ile | Leu | Gln | Asn | Leu | Thr | |
| | | | 100 | | | | | 105 | | | | | 110 | | | |

| CTC | CGC | ATT | CAA | GTA | TCT | ATG | TTG | GGT | GCA | AAA | GGC | CAA | CCC | AGC | CCT | 384 |
|---|---|---|---|---|---|---|---|---|---|---|---|---|---|---|---|---|
| Leu | Arg | Ile | Gln | Val | Ser | Met | Leu | Gly | Ala | Lys | Gly | Gln | Pro | Ser | Pro | |
| | | 115 | | | | | 120 | | | | | 125 | | | | |

| GGT | GAG | GGA | ACA | CGA | CCA | CGA | GAA | TCA | AAC | GAC | CCC | AAC | GCC | ACC | CGA | 432 |
|---|---|---|---|---|---|---|---|---|---|---|---|---|---|---|---|---|
| Gly | Glu | Gly | Thr | Arg | Pro | Arg | Glu | Ser | Asn | Asp | Pro | Asn | Ala | Thr | Arg | |
| 130 | | | | | 135 | | | | | 140 | | | | | | |

| CGT | GCC | CGC | TCC | CGC | TCC | CGG | GGA | CGT | GAA | GCA | AAG | AAA | GTG | CAA | ATT | 480 |
|---|---|---|---|---|---|---|---|---|---|---|---|---|---|---|---|---|
| Arg | Ala | Arg | Ser | Arg | Ser | Arg | Gly | Arg | Glu | Ala | Lys | Lys | Val | Gln | Ile | |
| 145 | | | | 150 | | | | | 155 | | | | | 160 | | |

| TCT | GAT | TAA | | | | | | | | | | | | | | 489 |
|---|---|---|---|---|---|---|---|---|---|---|---|---|---|---|---|---|
| Ser | Asp | | | | | | | | | | | | | | | |

(2) INFORMATION FOR SEQ ID NO: 2:

(i) SEQUENCE CHARACTERISTICS:
        (A) LENGTH: 162 amino acids
        (B) TYPE: amino acid
        (D) TOPOLOGY: linear (ii) MOLECULE TYPE: protein (xi) SEQUENCE DESCRIPTION: SEQ ID NO: 2:

| Met | Ser | Ala | Pro | Arg | Lys | Val | Arg | Leu | Pro | Ser | Val | Lys | Ala | Val | Asp |
|---|---|---|---|---|---|---|---|---|---|---|---|---|---|---|---|
| 1 | | | | 5 | | | | | 10 | | | | | 15 | |

| Met | Ser | Met | Glu | Asp | Met | Ala | Ala | Arg | Leu | Ala | Arg | Leu | Glu | Ser | Glu |
|---|---|---|---|---|---|---|---|---|---|---|---|---|---|---|---|
| | | | 20 | | | | 25 | | | | | 30 | | | |

| Asn | Lys | Ala | Leu | Lys | Gln | Gln | Val | Leu | Arg | Gly | Gly | Ala | Cys | Ala | Ser |
|---|---|---|---|---|---|---|---|---|---|---|---|---|---|---|---|
| | | 35 | | | | | 40 | | | | | 45 | | | |

| Ser | Thr | Ser | Val | Pro | Ser | Ala | Pro | Val | Pro | Pro | Pro | Glu | Pro | Leu | Thr |
|---|---|---|---|---|---|---|---|---|---|---|---|---|---|---|---|
| | 50 | | | | | 55 | | | | | 60 | | | | |

| Ala | Arg | Gln | Arg | Glu | Val | Met | Ile | Thr | Gln | Ala | Thr | Gly | Arg | Leu | Ala |
|---|---|---|---|---|---|---|---|---|---|---|---|---|---|---|---|
| 65 | | | | | 70 | | | | | 75 | | | | | 80 |

| Ser | Gln | Ala | Met | Lys | Lys | Ile | Glu | Asp | Lys | Val | Arg | Lys | Ser | Val | Asp |
|---|---|---|---|---|---|---|---|---|---|---|---|---|---|---|---|
| | | | | 85 | | | | | 90 | | | | | 95 | |

-continued

```
Gly Val Thr Thr Arg Asn Glu Met Glu Asn Ile Leu Gln Asn Leu Thr
            100             105                 110

Leu Arg Ile Gln Val Ser Met Leu Gly Ala Lys Gly Gln Pro Ser Pro
        115             120                 125

Gly Glu Gly Thr Arg Pro Arg Glu Ser Asn Asp Pro Asn Ala Thr Arg
    130             135             140

Arg Ala Arg Ser Arg Ser Arg Gly Arg Glu Ala Lys Lys Val Gln Ile
145             150             155                 160

Ser Asp
```